(12) United States Patent
Sehnert et al.

(10) Patent No.: US 11,464,475 B2
(45) Date of Patent: *Oct. 11, 2022

(54) SELF-CALIBRATING TECHNIQUE FOR X-RAY IMAGING SCANNERS

(71) Applicant: CARESTREAM HEALTH, INC., Rochester, NY (US)

(72) Inventors: William J. Sehnert, Fairport, NY (US); Yuan Lin, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/082,080

(22) Filed: Oct. 28, 2020

(65) Prior Publication Data

US 2021/0106304 A1    Apr. 15, 2021

Related U.S. Application Data

(63) Continuation of application No. 16/692,362, filed on Nov. 22, 2019, now Pat. No. 10,842,462, which is a continuation of application No. 15/971,213, filed on May 4, 2018, now Pat. No. 10,517,561.

(Continued)

(51) Int. Cl.
*A61B 6/00* (2006.01)
*A61B 6/03* (2006.01)
(Continued)

(52) U.S. Cl.
CPC ............. *A61B 6/582* (2013.01); *A61B 6/025* (2013.01); *A61B 6/032* (2013.01); *A61B 6/06* (2013.01);
(Continued)

(58) Field of Classification Search
CPC ....... A61B 6/025; A61B 6/032; A61B 6/0421; A61B 6/06; A61B 6/08; A61B 6/4405;
(Continued)

(56) References Cited

U.S. PATENT DOCUMENTS 8,821,017 B2  9/2014  Lalena et al.
10,517,561 B2  12/2019  Lin et al.
(Continued)

FOREIGN PATENT DOCUMENTS

WO    2016/003957 A2    1/2016

OTHER PUBLICATIONS

S. Ouadah et al., Self-Calibration of Cone-Beam CT Geometry Using 3D-2D Image Registration: Development and Application to Task-Based Imaging with a Robotic C-Arm, Proc. SPIE Int Soc Opt Eng., Feb. 21, 2015, doi: 10.1117/12.2082538, pp. 1-13.
(Continued)

*Primary Examiner* — Mark R Gaworecki

(57) ABSTRACT

A mobile radiography apparatus has radio-opaque markers, each marker coupled to a portion of the mobile radiography apparatus, wherein each of the markers is in a radiation path that extends from an x-ray source or x-ray sources. A detector is mechanically uncoupled from the x-ray source or x-ray sources for positioning behind a patient. Processing logic is configured to calculate a detector position with relation to the x-ray source or x-ray sources according to identified marker positions in acquired projection images, and to reconstruct a volume image according to the acquired projection images.

20 Claims, 8 Drawing Sheets

Related U.S. Application Data

(60) Provisional application No. 62/507,288, filed on May 17, 2017, provisional application No. 62/598,519, filed on Dec. 14, 2017.

(51) Int. Cl.

| | |
|---|---|
| *A61B 6/02* | (2006.01) |
| *A61B 90/30* | (2016.01) |
| *A61B 6/06* | (2006.01) |
| *A61B 6/08* | (2006.01) |
| *A61B 90/00* | (2016.01) |
| *A61B 6/04* | (2006.01) |

(52) U.S. Cl.
CPC .............. *A61B 6/08* (2013.01); *A61B 6/4405* (2013.01); *A61B 6/5205* (2013.01); *A61B 6/547* (2013.01); *A61B 6/584* (2013.01); *A61B 6/588* (2013.01); *A61B 90/39* (2016.02); *A61B 6/0421* (2013.01); *A61B 2090/3966* (2016.02)

(58) Field of Classification Search
CPC ....... A61B 6/5205; A61B 6/547; A61B 6/582; A61B 6/584; A61B 6/588; A61B 90/39; A61B 90/3966
See application file for complete search history.

(56) References Cited

U.S. PATENT DOCUMENTS

| | | | |
|---|---|---|---|
| 10,743,822 B2 | 8/2020 | Simon et al. | |
| 10,842,462 B2 * | 11/2020 | Sehnert | ............... A61B 6/547 |
| 2006/0039591 A1 | 2/2006 | Zettel et al. | |
| 2008/0095302 A1 | 4/2008 | Ruhrnschopf et al. | |
| 2011/0191084 A1 | 8/2011 | Cooke | |
| 2015/0043712 A1 | 2/2015 | Wang et al. | |
| 2016/0174915 A1 | 6/2016 | O'Dea et al. | |
| 2016/0278732 A1 | 9/2016 | Amiri | |
| 2018/0333131 A1 | 11/2018 | Lin | |
| 2020/0000426 A1 | 1/2020 | Simon et al. | |
| 2021/0113176 A1 | 4/2021 | Sehnert et al. | |
| 2021/0177371 A1 | 6/2021 | Wang et al. | |

OTHER PUBLICATIONS

Yuan Lin and Ehsan Samei, "A fast poly-energetic iterative FBP algorithm," Physics in Medicine and Biology 59, 2014, pp. 1655-1678.

Yuan Lin and Ehsan Samei, "An efficient polyenergetic SART (pSART) reconstruction algorithm for quantitative myocardial CT perfusion," Medical Physics, 41(2), Feb. 2014, pp. 021911-1-021911-14.

F. Edward Boas and Dominik Fleischmann, "CT artifacts: Causes and reduction techniques," Imaging Med. (2012), 4(2), pp. 229-240.

Donghoon Lee et al., "Restoration of Full Data from Sparse Data in Low-Dose Chest Digital Tomosynthesis Using Deep Convolutional Neural Networks," Journal of Digital Imaging, Vo. 32, No. 3, Sep. 20, 2018, pp. 489-498.

International Search Report dated Apr. 30, 2021 for International Application No. PCT/US2021/0138879, 2 pages.

\* cited by examiner

SELF-CALIBRATING TECHNIQUE FOR X-RAY IMAGING SCANNERS

CROSS REFERENCE TO RELATED APPLICATIONS

This application is a continuation patent application of U.S. patent application Ser. No. 16/692,362, filed on Nov. 22, 2019, entitled SELF-CALIBRATING TECHNIQUE FOR X-RAY IMAGING SCANNERS, in the name of Lin, et al., which is a continuation patent application of U.S. patent application Ser. No. 15/971,213, filed on May 4, 2018, entitled SELF-CALIBRATING TECHNIQUE FOR X-RAY IMAGING SCANNERS, in the name of Lin, et al., which claims the benefit of U.S. Provisional Application U.S. Ser. No. 62/507,288, provisionally filed on May 17, 2017, entitled SELF-CALIBRATING TECHNIQUE FOR X-RAY IMAGING SCANNERS, in the name of Lin et al., and U.S. Provisional Application U.S. Ser. No. 62/598,519, provisionally filed on Dec. 14, 2017, entitled SELF-CALIBRATING TECHNIQUE FOR X-RAY IMAGING SCANNERS, in the names of Lin et al., which are both hereby incorporated herein by reference in their entirety.

TECHNICAL FIELD

The disclosure relates generally to the field of medical imaging, and in particular to mobile radiographic imaging apparatus. More particularly, this disclosure relates to a simple and reliable self-calibrating technique for mobile X-ray imaging scanners.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the relative orientations of the x-ray tube, patient and detector. This is usually accomplished by either moving both the detector and x-ray source or by fixing the position of the detector (source) and moving the x-ray source (detector). Three-dimensional data is reconstructed from the captured projections in the form of a number of slices through the patient anatomy, each parallel to the detector plane. A consequence of limited angular scanning is that the in-depth resolution is much lower than the in-plane resolution of the reconstructed object.

Reconstruction of volumetric data from a tomosynthesis system requires knowledge of the underlying capture geometry, including the orientation and position of the detector, the movement and position of the source and potential patient motion. Precise geometric information of the imaging system (orientation of the X-ray detector, and locations of the X-ray tube and X-ray detector during 2D projection image acquisition) affect the image quality of the reconstructed images. Mismapping between object space and the acquired 2D projection images can degrade spatial resolution and lead to image artifacts (e.g., ring artifacts).

In a conventional tomosynthesis system, many of the geometric variables are known, as the detector position is precisely specified and the relationship between source and detector is also well established. For stationary imaging scanners, acquisition geometry is fixed by the mechanical coupling of source and detector, such as through a C-arm or other type of gantry arrangement. Calibration of this geometry is straightforward, using a calibration phantom prior to image acquisition.

For a bed-side tomosynthesis system using mobile radiography apparatus, however, the detector is mechanically uncoupled from the source. Thus, the capture geometry is not fixed by system mechanics and can be difficult to determine with the desired accuracy. Mobile x-ray imaging scanners used for tomosynthesis are designed for seriously ill patients who cannot walk to, or stand in front of, stationary imaging scanners having fixed geometry. Instead, in order to image these patients, the detector is often manually positioned under the bed-ridden patient. In this acquisition environment, without the benefit of mechanically fixed source-to-detector geometry, other approaches are needed in order to accurately determine the geometry information in real time.

There is a need for a calibration utility that is suited to estimate the geometry of a mobile radiography system used for tomosynthesis or other 3D volume imaging and that overcomes the aforementioned limitations.

SUMMARY

An aspect of the present application is to advance the art of radiography 3D volume imaging. Another aspect of this disclosure to address in whole or in part, at least the foregoing and other deficiencies in the related art. It is another aspect of this application to provide in whole or in part, at least the advantages described herein.

Another aspect of the application is to provide methods and/or apparatus by which mobile radiography carts can additionally provide 3D imaging capabilities with more accurate source/detector calibration.

Another aspect of the application is to provide methods and/or apparatus embodiments by which mobile radiography carts can acquire projection images and generate the reconstruction of three-dimensional tomographic and tomosynthesis images.

Another aspect of the application is to provide methods and/or apparatus embodiments by which mobile radiography carts can acquire x-ray 2D projection images and generate the reconstruction of two-dimensional or three-dimensional volume images, where an imaging geometry of x-ray source positions to a radiographic detection array is not known beforehand.

These objects are given only by way of illustrative example, and such objects may be exemplary of one or more embodiments of the invention. Other desirable objectives and advantages inherently achieved by the method and apparatus described herein may occur or become apparent to those skilled in the art. The invention is defined by the appended claims.

According to one aspect of the disclosure, there is provided a mobile radiography apparatus comprising: a plurality of radio-opaque markers, each marker coupled to a portion of an x-ray head of the mobile radiography apparatus, wherein each of the markers is in a radiation path that extends from at least one x-ray source; a detector that is mechanically uncoupled from the at least one x-ray source for positioning behind a patient; and processing logic configured to: (i) calculate detector position with relation to the at least one x-ray source according to identified marker positions in acquired projection images; (ii) remove marker indications in the acquired projection images; (iii) reconstruct a volume image according to the acquired projection images; and (iv) display one or more portions of the reconstructed volume image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1:
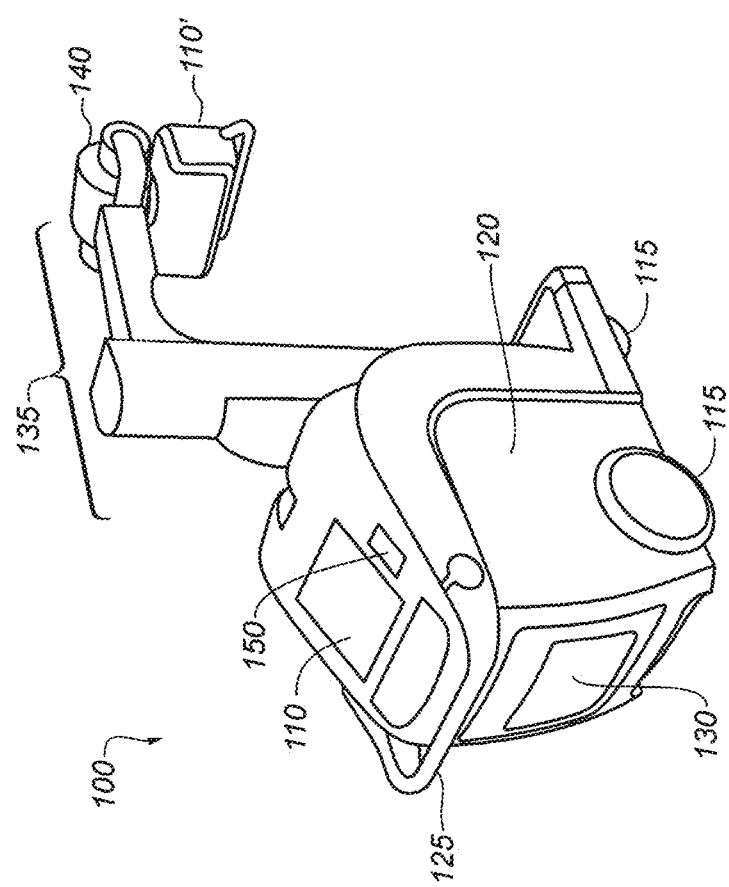
FIG. 1 is a diagram that shows a perspective view of a mobile radiography unit for use as a portable imaging system for tomosynthesis or other volume imaging.

The following is a description of exemplary embodiments of the invention, reference being made to the drawings in which the same reference numerals identify the same elements of structure in each of the several figures. Where they are used, the terms "first", "second", and so on, do not necessarily denote any ordinal or priority relation, but may be used for more clearly distinguishing one element or time interval from another.

Portable radiographic systems are routinely used in hospitals. Compared to standard projection radiography, volume imaging apparatus such as tomosynthesis apparatus provide improved depiction of fine details not visible in normal radiographs due to overlying structures. These benefits provide an impetus to develop portable volume imaging systems that can be utilized in the intensive care unit, emergency department, and operating rooms, where moving the patient is either impracticable or ill-advised due to the risk of harm to the patient.

The image quality of the reconstruction depends upon accurate knowledge of the acquisition scan geometry, including spatial and angular positions of the x-ray source and detector for each projection. Uncertainties in the scan geometry can lead to artifacts and/or blurring in the reconstructed object. The development of portable volume imaging systems has been hampered by difficulties in accurately determining the acquisition scan geometry. There remains a need for improved X-ray volume imaging systems that can be made portable and still provide reliable clinical images and data.

Reference is hereby made to an article by S. Quadah, J. W. Stayman, G. J. Gang, A. Uneri. T. Ehtiati, and J. H. Siewerdsen entitled "Self-calibration of cone-beam CT geometry using 3D-2D image registration" in *Phys. Med. Biol.* 2016, Apr. 7; pp. 2613-2632.

Reference is made to commonly assigned U.S. Pat. No. 8,821,017 (Lalena) entitled PROJECTOR AS COLLIMATOR LIGHT, incorporated herein in its entirety by reference.

FIG. 1 is a diagram that shows a perspective view of a mobile radiography unit that can use portable radiographic detectors or flat panel detectors that are mechanically uncoupled from the radiation source according to embodiments of the application. The exemplary mobile x-ray or radiographic apparatus of FIG. 1 can be employed for digital radiography (DR) and/or tomosynthesis or tomographic imaging. As shown in FIG. 1, a mobile radiography apparatus 100 can include a moveable transport frame 120 that includes a first display 110 and an optional second display 110' to display relevant information such as obtained images and related data. As shown in FIG. 1, the second display 110' can be pivotably mounted at the x-ray source, x-ray tube, or x-ray head 140 to be viewable/touchable from a 360 degree area.

The displays 110, 110' can implement or control (e.g., touch screens) functions such as generating, storing, transmitting, modifying, and printing of the obtained image(s) and can include an integral or separate control panel (not shown) to assist in implementing functions such as generating, storing, transmitting, modifying, and printing of obtained image(s). An optional touchpad 150 allows support functions such as operator identification.

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area (e.g., disposed on the frame 120) configured to removably retain at least one digital radiography (DR) detector. The storage area can be configured to hold a plurality of detectors and can also be configured to hold one size or multiple sizes of DR detectors.

Still referring to FIG. 1, a control logic processor 130 provides the control logic for image processing and identification of the position of the detector relative to the x-ray source. Image processing can be provided by a processor that is part of mobile radiography apparatus 100 itself, or can be provided by one or more external computers and other processors networked in signal communication with mobile radiography apparatus 100.

Mounted to frame 120 is a support column 135 that supports x-ray head 140, also called an x-ray tube, tube head, or generator, that includes the x-ray source and that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In addition, the support column is rotatably attached to the moveable frame 120. In another embodiment, the tube head 140 can be rotatably coupled to the support column 135. In another exemplary embodiment, an articulated member of the support column that bends at a joint mechanism can allow movement of the x-ray tube head 140 over a range of vertical and horizontal positions. Height settings for the x-ray tube head 140 can range from low height for imaging feet and lower extremities to shoulder height and above for imaging the upper body portions of patients in various positions.

Figure 2:
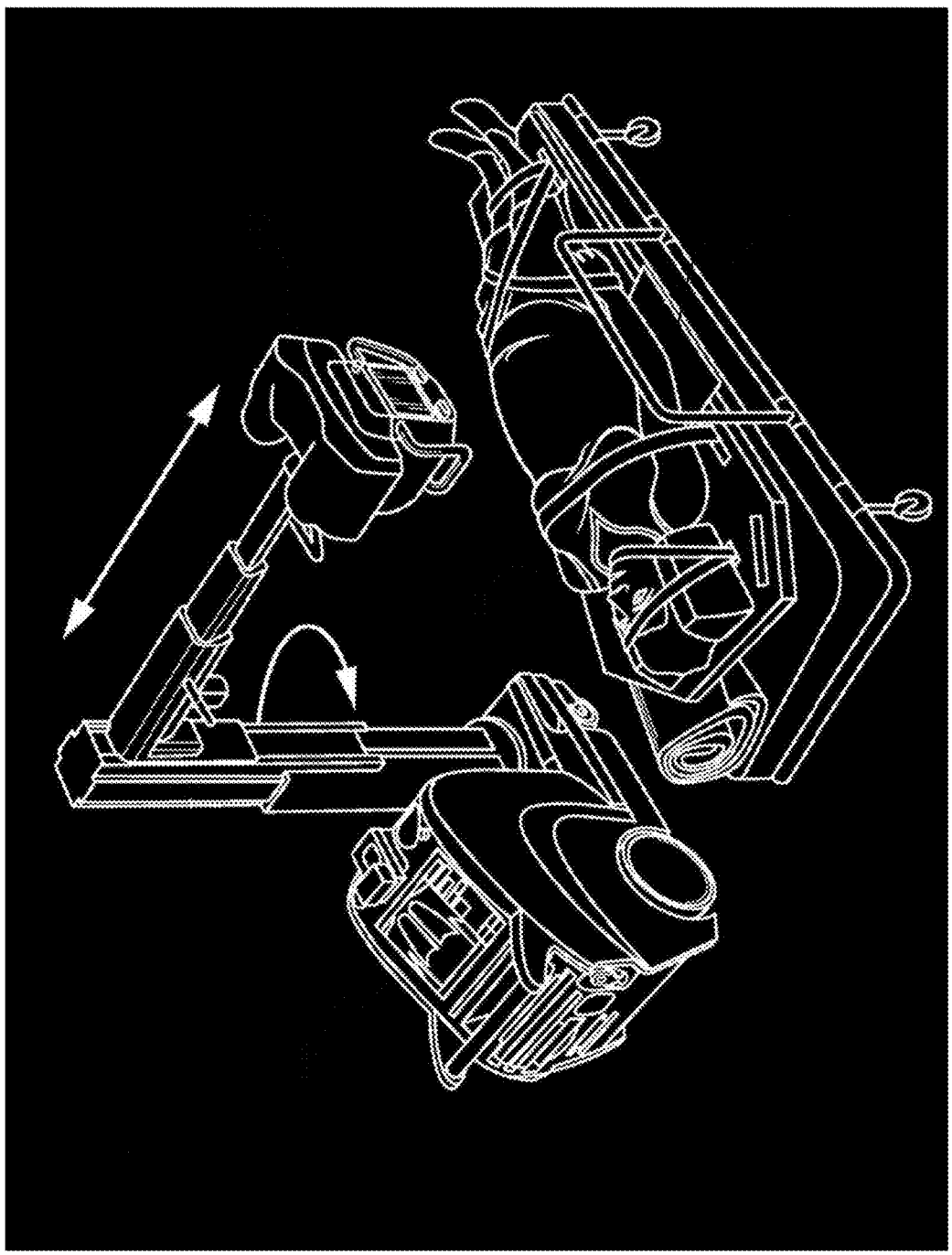
FIG. 2 is a perspective view that shows a mobile radiography apparatus in position for volume imaging.

The perspective view of FIG. 2 shows mobile radiography apparatus 100 in position for tomosynthesis or tomographic imaging. A patient 14 is lying flat on a bed or stretcher with a detector 20 fitted behind the patient 14 with respect to the x-ray source. There is no inherent mechanical linkage or alignment between x-ray head 140 and detector 20 and conventional calibration of source/detector geometry prior to exposure is not feasible.

Figure 3A:
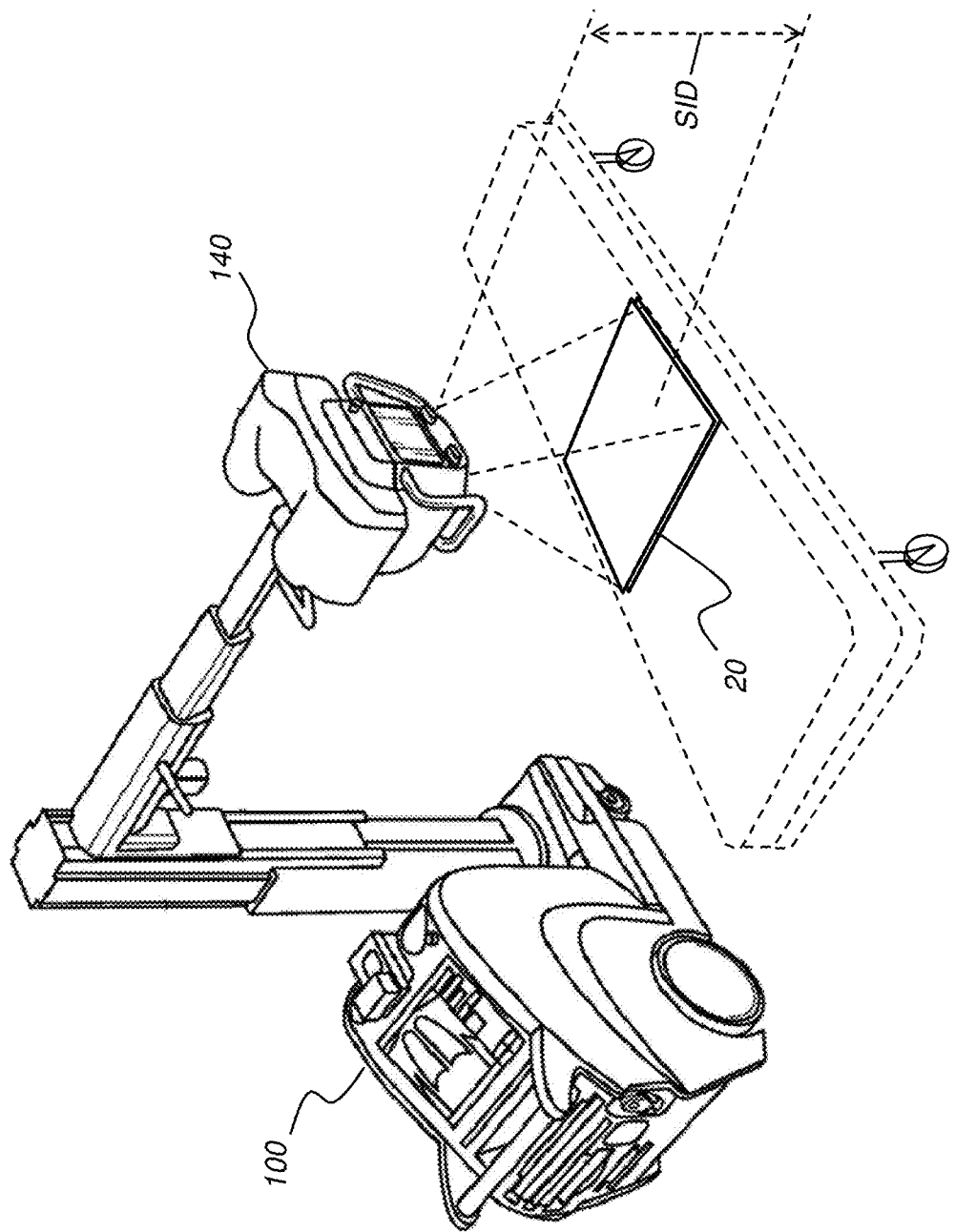
FIG. 3A is a perspective view that shows aspects of the image capture metrics and behavior that relate to geometric calibration for mobile radiology apparatus when used for tomosynthesis and other volume imaging.
Figure 3B:
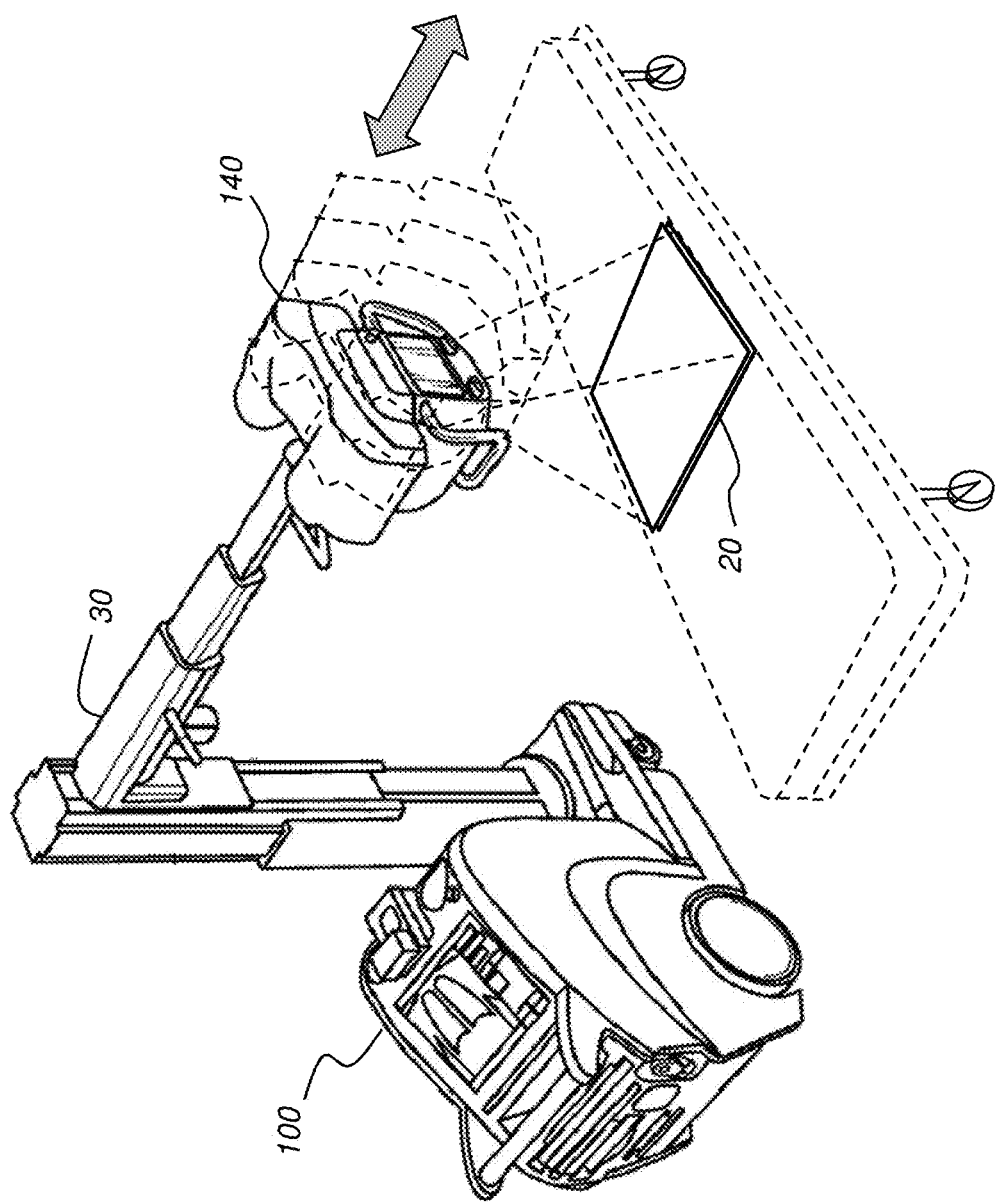
FIG. 3B is a perspective view that shows additional aspects of the image capture metrics and x-ray head translation related to geometric calibration for mobile radiology apparatus when used for tomosynthesis and other volume imaging.

The perspective views of FIGS. 3A and 3B show aspects of the image capture metrics and behavior that relate to geometric calibration for mobile radiology apparatus 100 when used for tomosynthesis or other volume imaging. A source-to-image distance SID can be approximated based on known factors, such as bed height and column height for radiography apparatus 100. Even where the SID can be accurately identified, however, there are additional calibration metrics that must be known. These include factors such as skew of the detector 20 relative to the x-ray source as shown in FIG. 3A and the relative travel path of the source and detector as successive images are acquired, as shown for linear travel by a transport apparatus 30 in FIG. 3B.

Figure 4:
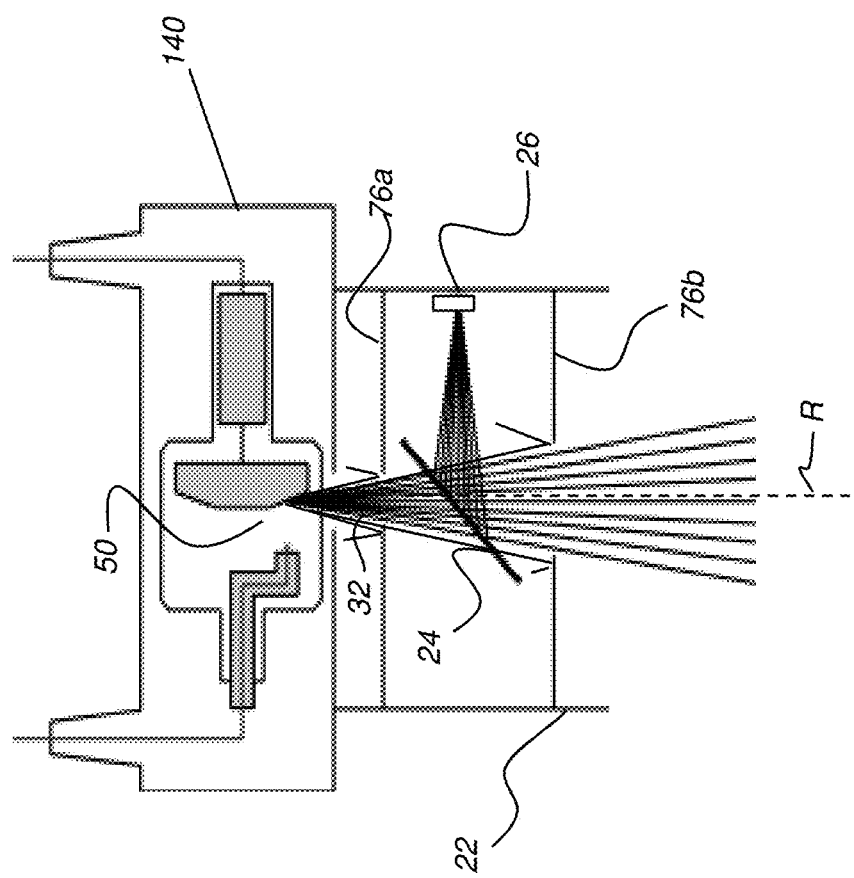
FIG. 4 is a schematic cross-section of a conventional x-ray tube head.

The cutaway cross-sectional schematic view of FIG. 4 shows conventional x-ray tube head 140 having an x-ray radiation source 50 with a collimator 22 and a collimator light 26. Collimator 22 typically has two collimator sections 76*a* and 76*b*, each with blades positioned for shaping the output radiation beam. A collimator light 26, typically a light bulb or light emitting diode (LED) or other solid-state light source, mounts inside collimator 22 and serves as a guide for aiming orientation of the x-ray head 140. A mirror 24, essentially transparent to x-rays but reflective to visible light, combines the light path of collimator light 26 with the radiation path R of x-ray beam 32 that extends from the x-ray source, so that the cross-sectional area of the light beam from collimator light 26 matches the cross-sectional area of the collimated radiation beam that is emitted from x-ray head 140.

Figure 5:
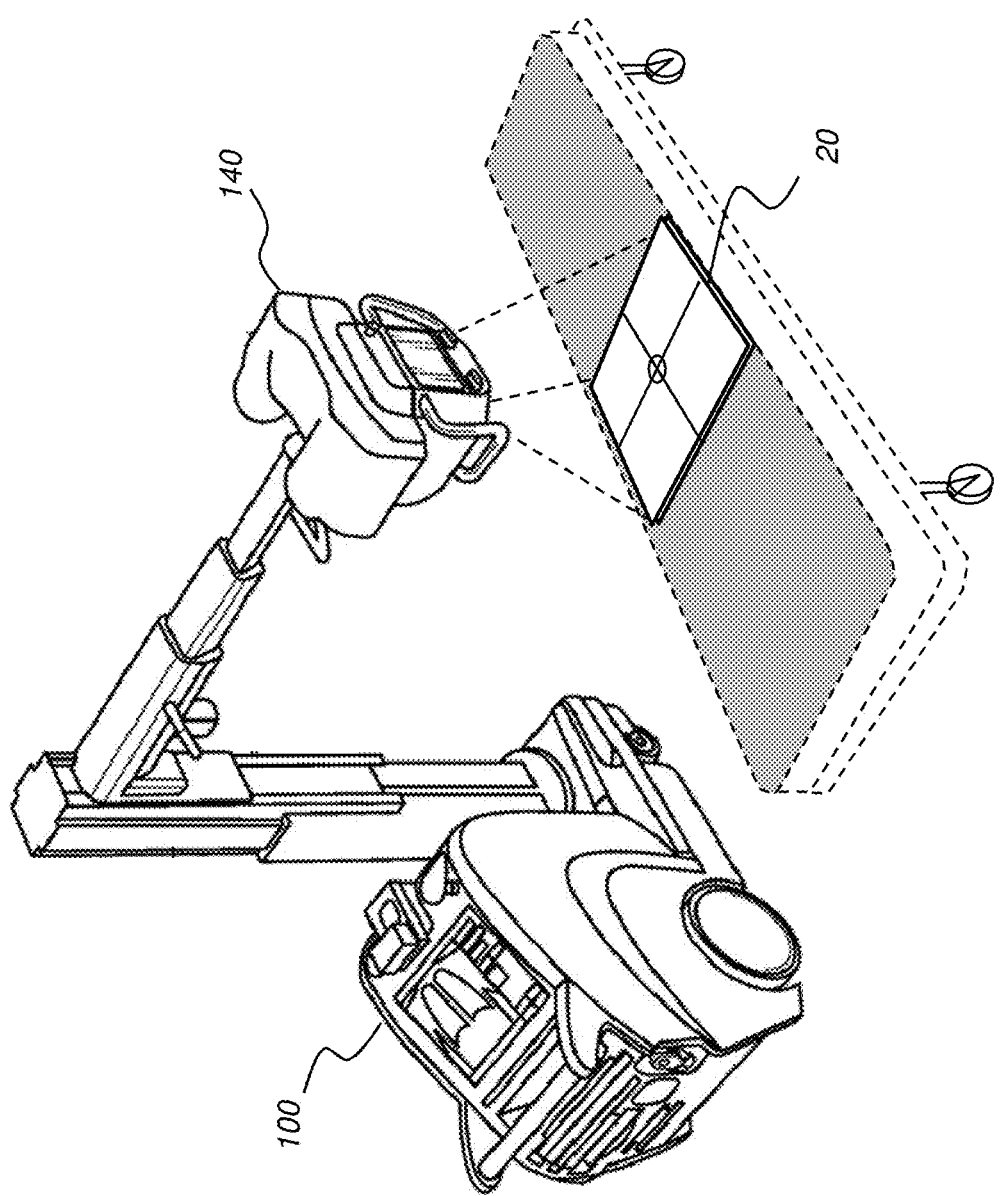
FIG. 5 is a perspective view showing the function of a collimator light, which projects a pattern of light to assist registration of the patient to the source.

The perspective view of FIG. 5 shows the function of collimator light 26, which typically projects a pattern of light to assist registration of the patient to the source so that the collimated beam is directed to the subject region that is properly within the perimeter of the detector 20. As has been emphasized, however, it is generally not feasible to identify the exact position and skew orientation of detector 20 relative to the beam from x-ray head 140 for mobile radiography applications, for reasons such as detector placement and condition of the patient.

According to embodiments of the present disclosure, geometric calibration of the source and detector is performed using the acquired radiography image content. Radio-opaque markers are disposed within x-ray head 140, at fixed positions along radiation path R. The image content that is acquired at the x-ray detector 20 includes the markers.

The position of the markers in the acquired x-ray image relates directly to the relative geometry of the x-ray source 50 and detector 20 and can be used to calculate this geometry with sufficient accuracy to provide a faithful reconstruction of depth information for the imaged anatomy.

Figure 6:
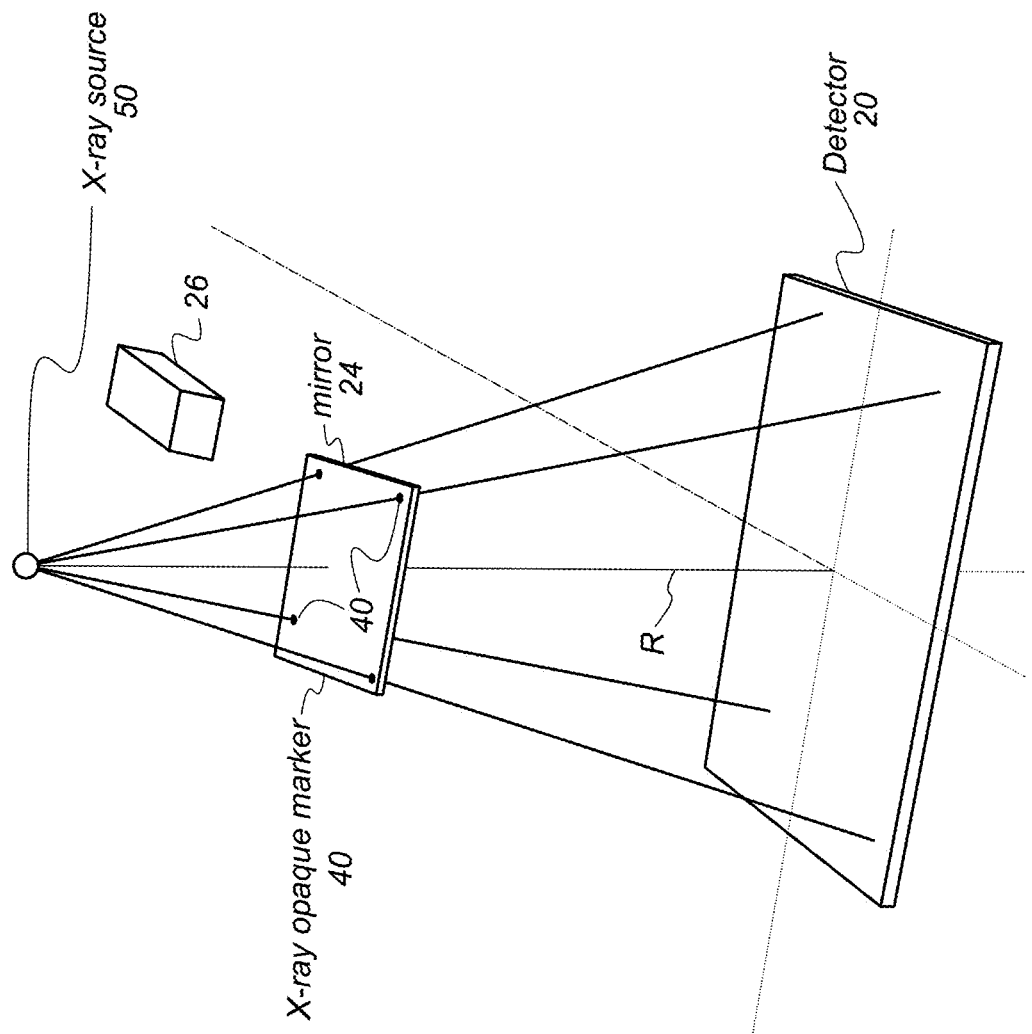
FIG. 6 is a schematic diagram showing components of a self-calibrating apparatus for a mobile radiography apparatus.

Referring to the simplified schematic diagram of FIG. 6, mirror 24 of x-ray head 140 is shown in relation to the position of collimator light 26 and x-ray source 50. Mirror 24 has been modified to include a set of radio-opaque markers 40, each marker 40 disposed in path R of the x-ray radiation directed toward detector 20. Because each marker is radio-opaque, the markers 40 are detected in the x-ray image content from detector 20. The pattern of markers 40 that are imaged by detector 20 and the overall geometry of the detected pattern can provide sufficient information for an accurate calibration of detector 20 to x-ray source 50.

It should be noted that, while mirror 24 can be a convenient vehicle for mounting of the radio-opaque markers within x-ray head 140, other components that lie in the radiation path R can alternately be used, such as filters, for example. The markers can be coupled to a suitable radio transparent support surface or to some other feature that is in the path of the radiation beam and collimator light.

There are a number of considerations that relate to marker use for geometric calibration of a mobile radiography apparatus, including the following:

(i) Marker positioning along the periphery of the radiation field. Peripheral positions of markers 40 with respect to the detector imaging area are generally advantageous. Anatomical information of interest is generally centered in the image area; markers 40 along the edges or outside of the imaged area are less likely to interfere with 3D reconstruction.

(ii) Fixed positioning. Marker positions are fixed in the housing of the x-ray head 140 and do not change with adjustment of head 140 position. If markers 40 are provided on the mirror, the mirror should be in a fixed position within the head.

(iii) Calibration of markers 40 to head 140. An initial geometric calibration of markers 40 position to the head 140 and x-ray source 50 is performed as a setup procedure for the mobile radiography apparatus, prior to use of markers 40 for source/detector calibration for a patient image.

(iv) Shadows. Markers 40 generate shadows in the acquired projection image. Additional image processing steps are needed in order to remove the marker shadows following geometric calibration. Well-known image processing procedures such as segmentation, interpolation, and in-painting can be employed to compensate for shadow effects.

(v) High magnification factor. The geometry magnification factor for markers is significant. Thus, the markers 40 themselves should be made as small and distinct as possible.

(vi) Marker shape. Specially shaped markers 40 facilitate marker detection and removal from the projection images. For example, circular, triangular, or cross-shaped markers 40 may be advantaged. Although the marker shape may increase marker size, distinctive shapes can help to simplify detection of the center of the marker, allowing ready identification and removal.

(vii) Adjustable collimators. Depending on the design of x-ray head 140, collimators 22 may be adjustable. This factor must be taken into account for marker design and positioning. A specific collimator position may work best for subsequent detection and removal of marker effects.

Calibration of marker position (item (iii) above) can be performed by establishing precise positional coordinates for detector 20 relative to x-ray source 50 and acquiring image content from two or more exposures along the travel path of x-ray head 140. Calibration of marker position can then be calculated from positional and movement information from the resulting sequence of projection images, using well known methods of triangulation and projective geometry.

Using the initially calibrated marker 40 position with respect to x-ray source 50, metrics such as SID, skew, and planar orientation of the detector 20 can be readily computed using well-known projective geometry calculations.

Figure 7:
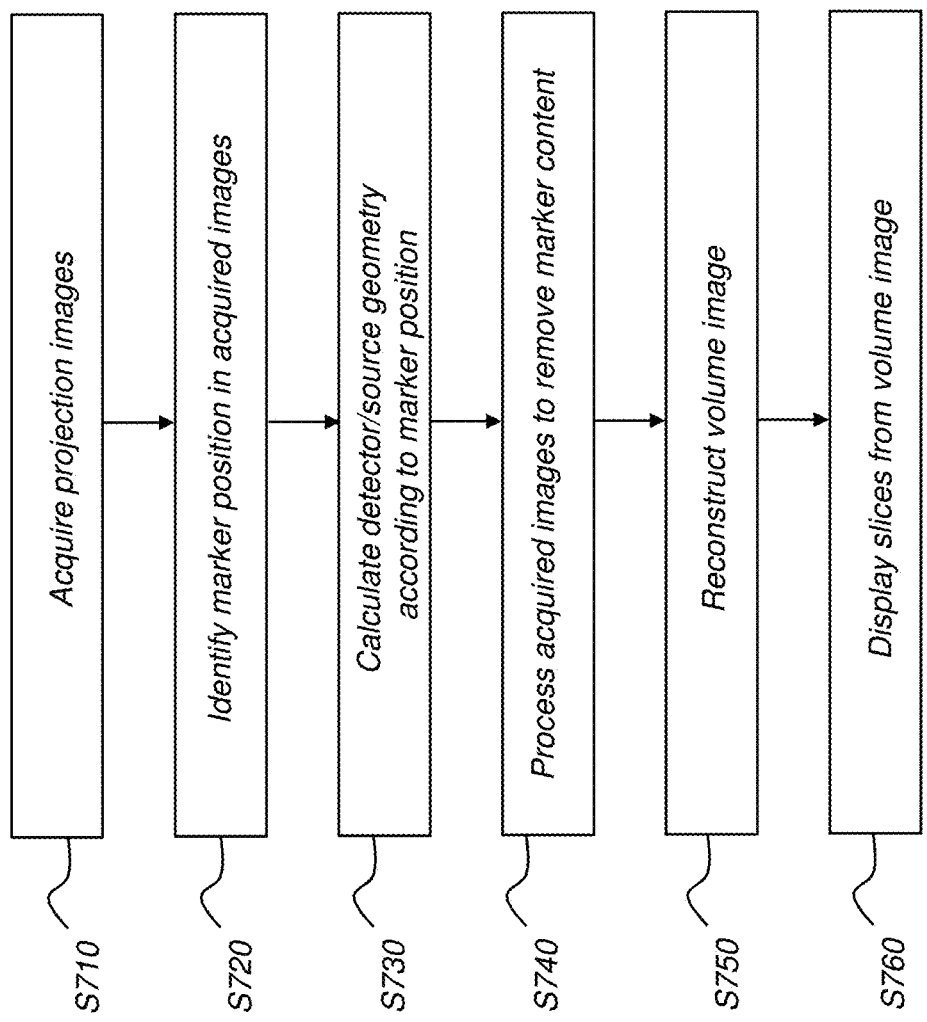
FIG. 7 is a logic flow diagram that shows a sequence for calibration of a mobile radiography apparatus having a detector that is not mechanically coupled to the x-ray source.

The logic flow diagram of FIG. 7 shows a sequence for calibration of a mobile radiography apparatus having a detector that is not mechanically coupled to the x-ray source and wherein (i) the apparatus is configured with markers and (ii) marker calibration to the x-ray source has been performed. A set of 2D projection images of the subject is acquired for processing in an image acquisition step S710. Marker positions in the projection images are then identified in an identification step S720. A calculation step S730 then calculates detector/source geometry based on identified marker position, using well known projective geometry processing. A cleanup step S740 is then executed, in which marker content is removed from the projection images. Cleanup step S740 can use interpolation, in-painting, and other well known processes in order to restore image content and remove marker shadows, as noted previously. This can be readily accomplished, since the markers have the same position in each acquired projection image. A reconstruction step S750 can then be executed in order to generate the 3D volume image from corrected 2D projection images. Reconstruction methods for tomography and tomosynthesis imaging are well known and include filtered back projection (FBP) and iterative reconstruction methods, allowing a number of processing sequences to be used for volume image reconstruction. 2D slices or other portions or projections of the generated 3D volume image can then be extracted and displayed in a display step S760.

According to an embodiment of the present disclosure, only a portion of the acquired projection images in a tomosynthesis series or tomography series are analyzed for marker position detection and calculation of source/detector geometry in step S730.

Using radio-opaque markers embedded along the radiation path and executing the process outlined with respect to FIG. 7, an embodiment of the present disclosure enables source/detector geometry to be calculated from the set of projection images that is acquired. Thus, embodiments of the present disclosure are advantageous for calibration use with mobile radiography apparatus and other radiography systems in which the imaging detector is mechanically uncoupled from the radiation source.

Markers 40 can be formed of lead or other radio-opaque material, including metals such as tungsten. Markers can be formed into beads or into some other suitable shape, such as a cross or circle, a square, a triangle, or some other shape and can be adhered, imprinted by deposition onto a radio-transparent surface, or otherwise coupled to a mirror, filter, or other permanent feature of the x-ray head 140. Markers 40 can be coupled to a radio-transparent support feature, such as a glass or plastic surface or feature, that is in the path of collimated energy from the x-ray source.

The following references are cited:
Yuan Lin and Ehsan Samei. "A FAST POLY-ENERGETIC FBP ALGORITHM", Physics in Medicine and Biology 59 (2014) pp. 1655-1678;
Yuan Lin and Ehsan Samei, "AN EFFICIENT POLYENERGETIC SART (pSART) RECONSTRUCTION ALGORITHM FOR QUANTITIVE MYOCARDIAL CT PERFUSION", Medical Physics, 41 (2) February 2014. pp. 021911-1 to 021911-14;
F. Edward Boas and Dominik Fleischmann, "CT ARTIFACTS: CAUSES AND REDUCTION TECHNIQUES", Imaging Med. (2012) 4 (2), 229-240, pp. 1-19;
US 2008/0095302 (Ruhrnschopf) titled "METHOD FOR HARDENING CORRECTION IN MEDICAL IMAGING";
WO 2016/003957 (Lin) titled "SPECTRAL ESTIMATION AND POLY-ENERGETIC RECONSTRUCTION METHODS AND X-RAY SYSTEMS" published on Jan. 7, 2016.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A mobile radiography apparatus comprising:
an x-ray source;
a plurality of radio-opaque markers disposed in a radiation path extending from the x-ray source to a radiographic detector mechanically uncoupled from the x-ray source; and
a processor programmed to calculate a position of the detector relative to the x-ray source according to positions of the radio-opaque markers in acquired projection images, and to reconstruct a volume image according to the acquired projection images.

2. The apparatus of claim 1, wherein one or more of the plurality of radio-opaque markers have a spherical shape.

3. The apparatus of claim 1, wherein one or more of the plurality of radio-opaque markers is formed by depositing radio-opaque material onto a surface.

4. The apparatus of claim 1, further comprising a collimator light and a mirror, wherein one or more of the plurality of radio-opaque markers is coupled to the mirror, and wherein the mirror is disposed in an illumination path of the collimator light.

5. The apparatus of claim 1, further comprising a radiolucent support disposed in the radiation path, wherein one or more of the plurality of radio-opaque markers is coupled to the radiolucent support.

6. The apparatus of claim 1, further comprising a transport apparatus for translating the x-ray source along a path to acquire a sequence of images of the patient using the x-ray source at different positions along the path.

7. The apparatus of claim 1, wherein the control logic processor is further programmed to remove an image of the radio-opaque markers from the acquired projection images.

8. The apparatus of claim 1, further comprising an x-ray head, wherein the plurality of radio-opaque markers are rigidly attached to the x-ray head.

9. A mobile radiography apparatus comprising:

an x-ray source;

a plurality of radio-opaque markers disposed in an x-ray beam extending from the x-ray source to a radiographic detector mechanically uncoupled from the x-ray source; and a processor programmed to calculate a position of the detector relative to the x-ray source according to positions of the radio-opaque markers in projection images captured by the detector, and to reconstruct a volume image according to the captured projection images.

10. The apparatus of claim 9, wherein one or more of the plurality of radio-opaque markers have a spherical shape.

11. The apparatus of claim 9, wherein one or more of the plurality of radio-opaque markers is formed by depositing radio-opaque material onto a surface.

12. The apparatus of claim 9, further comprising a collimator light and a mirror, wherein one or more of the plurality of radio-opaque markers is coupled to the mirror, and wherein the mirror is disposed in an illumination path of the collimator light.

13. The apparatus of claim 9, further comprising a radiolucent support disposed in the x-ray beam, wherein one or more of the plurality of radio-opaque markers is coupled to the radiolucent support.

14. The apparatus of claim 9, further comprising a transport apparatus for translating the x-ray source along a path to capture a sequence of images of a patient using the x-ray source at different positions along the path.

15. A method of operating a mobile radiography apparatus having an x-ray source, the method comprising:

positioning a plurality of radio-opaque markers in a radiation beam extending from the x-ray source to a subject;

using the x-ray source and a detector, acquiring a sequence of projection images of the subject;

processing each of the acquired projection images of the subject to identify a position of one or more of the radio-opaque markers within the acquired projection images;

using the identified position of the one or more radio-opaque markers, calculating a position of the detector with respect to the x-ray source; and reconstructing a volume image of the subject using the acquired projection images according to the calculated position of the detector.

16. The method of claim 15, further comprising processing the acquired projection images to remove the one or more radio-opaque markers within the acquired projection images.

17. The method of claim 16, wherein the step of processing the acquired projection images to remove the one or more radio-opaque markers comprises using in-painting or interpolation.

18. The method of claim 15, further comprising rigidly attaching the plurality of radio-opaque markers to a portion of the mobile radiography apparatus.

19. The method of claim 18, wherein the step of rigidly attaching the plurality of radio-opaque markers comprises using a rigid radiolucent support arm.

20. The method of claim 15, further comprising forming one or more of the plurality of radio-opaque markers using lead or tungsten in a shape of a sphere, a cross, a circle, a square, or a triangle.

\* \* \* \* \*